United States Patent
McDaniel

(10) Patent No.: US 9,101,733 B2
(45) Date of Patent: Aug. 11, 2015

(54) CATHETER WITH BIASED PLANAR DEFLECTION

(75) Inventor: Benjamin D. McDaniel, Irvine, CA (US)

(73) Assignee: Biosense Webster, Inc., Diamond Bar, CA (US)

( * ) Notice: Subject to any disclaimer, the term of this patent is extended or adjusted under 35 U.S.C. 154(b) by 697 days.

(21) Appl. No.: 12/569,779

(22) Filed: Sep. 29, 2009

(65) Prior Publication Data

US 2011/0077498 A1    Mar. 31, 2011

(51) Int. Cl.
| | |
|---|---|
| *A61M 25/092* | (2006.01) |
| *A61M 25/00* | (2006.01) |
| *A61B 18/14* | (2006.01) |
| *A61M 25/01* | (2006.01) |
| *A61B 19/00* | (2006.01) |
| *A61B 5/042* | (2006.01) |
| *A61B 18/00* | (2006.01) |

(52) U.S. Cl.
CPC ........ *A61M 25/0052* (2013.01); *A61B 18/1492* (2013.01); *A61M 25/0144* (2013.01); *A61B 5/042* (2013.01); *A61B 2018/00023* (2013.01); *A61B 2018/00839* (2013.01); *A61B 2019/5251* (2013.01); *A61B 2218/002* (2013.01); *A61B 2218/007* (2013.01); *A61M 25/0147* (2013.01); *A61M 2025/004* (2013.01); *A61M 2025/015* (2013.01)

(58) Field of Classification Search
USPC ......... 600/374, 393, 146, 95.04, 373; 606/41; 604/146, 95.04
See application file for complete search history.

(56) References Cited

U.S. PATENT DOCUMENTS

| | | |
|---|---|---|
| 2,498,692 A | 2/1950 | Mains |
| 3,371,573 A | 3/1968 | Koreki et al. |

(Continued)

FOREIGN PATENT DOCUMENTS

| | | |
|---|---|---|
| EP | 0 689 851 A1 | 1/1996 |
| EP | 1 120 082 A1 | 8/2001 |

(Continued)

OTHER PUBLICATIONS

European Search Report dated Jan. 21, 2011 (search completed Jan. 11, 2011) for EP Application No. 10251664.8, 13 pages.

(Continued)

*Primary Examiner* — Linda Dvorak
*Assistant Examiner* — Jocelyn D Ram
(74) *Attorney, Agent, or Firm* — Christie, Parker & Hale, LLP

(57) ABSTRACT

An improved steerable catheter with biased, in-plane bi-directional deflection has an elongated catheter body, a deflectable intermediate section having a tubing with at least a first and a second off-axis opposing lumens for puller wires that define a plane of deflection, and a control handle at a proximal end of the catheter body. The deflectable intermediate section includes at least two elongated bias members that extend along the length and lie on a plane perpendicular to the plane of deflection so as to resist flexure outside of the plane of deflection. In a more detailed embodiment, the deflectable intermediate section has an integrated tubular construction that includes an inner layer, a braided mesh surrounding the inner layer and an outer layer, where the bias members can be situated between the inner layer and the braided mesh, or between the braided mesh and the outer layer.

20 Claims, 11 Drawing Sheets

(56) References Cited

U.S. PATENT DOCUMENTS

| | | | | |
|---|---|---|---|---|
| 3,470,876 A | * | 10/1969 | Barchilon | 604/95.04 |
| 3,783,736 A | | 1/1974 | Richardson | |
| 4,619,643 A | | 10/1986 | Bai | |
| 4,686,963 A | | 8/1987 | Cohen et al. | |
| 4,934,340 A | * | 6/1990 | Ebling et al. | 600/151 |
| 5,195,968 A | | 3/1993 | Lundquist et al. | |
| 5,199,950 A | * | 4/1993 | Schmitt et al. | 604/95.04 |
| 5,203,380 A | | 4/1993 | Chikama | |
| 5,254,088 A | | 10/1993 | Lundquist et al. | |
| 5,257,571 A | | 11/1993 | Richardson | |
| RE34,502 E | | 1/1994 | Webster, Jr. | |
| 5,318,525 A | | 6/1994 | West et al. | |
| 5,374,245 A | | 12/1994 | Mahurkar | |
| 5,391,199 A | | 2/1995 | Ben-Haim | |
| 5,395,327 A | | 3/1995 | Lundquist et al. | |
| 5,395,328 A | * | 3/1995 | Ockuly et al. | 604/528 |
| 5,443,489 A | | 8/1995 | Ben-Haim | |
| 5,456,674 A | | 10/1995 | Bos et al. | |
| 5,480,422 A | | 1/1996 | Ben-Haim | |
| 5,500,012 A | | 3/1996 | Brucker et al. | |
| 5,507,725 A | | 4/1996 | Savage et al. | |
| 5,545,200 A | | 8/1996 | West et al. | |
| 5,546,951 A | | 8/1996 | Ben-Haim | |
| 5,558,091 A | | 9/1996 | Acker et al. | |
| 5,568,809 A | | 10/1996 | Ben-haim | |
| 5,674,197 A | | 10/1997 | van Muiden et al. | |
| 5,676,653 A | * | 10/1997 | Taylor et al. | 604/95.04 |
| 5,715,817 A | | 2/1998 | Stevens-Wright et al. | |
| 5,820,591 A | | 10/1998 | Thompson et al. | |
| 5,824,031 A | | 10/1998 | Cookston et al. | |
| 5,855,560 A | | 1/1999 | Idaomi et al. | |
| 5,897,529 A | | 4/1999 | Ponzi | |
| 5,906,590 A | | 5/1999 | Hunjan et al. | |
| 5,964,757 A | | 10/1999 | Ponzi | |
| 6,064,908 A | | 5/2000 | Muller et al. | |
| 6,123,699 A | | 9/2000 | Webster, Jr. | |
| 6,171,277 B1 | | 1/2001 | Ponzi | |
| 6,183,463 B1 | | 2/2001 | Webster, Jr. | |
| 6,198,974 B1 | * | 3/2001 | Webster, Jr. | 607/122 |
| 6,201,387 B1 | | 3/2001 | Govari | |
| 6,210,407 B1 | | 4/2001 | Webster | |
| 6,267,746 B1 | | 7/2001 | Bumbalough | |
| 6,402,719 B1 | | 6/2002 | Ponzi et al. | |
| 6,450,948 B1 | | 9/2002 | Matsuura et al. | |
| 6,522,933 B2 | | 2/2003 | Nguyen | |
| 6,569,114 B2 | * | 5/2003 | Ponzi et al. | 604/95.04 |
| 6,602,242 B1 | * | 8/2003 | Fung et al. | 604/528 |
| 6,837,867 B2 | * | 1/2005 | Kortelling | 604/95.04 |
| 6,913,594 B2 | | 7/2005 | Coleman et al. | |
| 7,018,372 B2 | | 3/2006 | Casey et al. | |
| 7,377,906 B2 | | 5/2008 | Selkee | |
| 8,070,693 B2 | * | 12/2011 | Ayala et al. | 600/585 |
| 8,182,467 B2 | * | 5/2012 | Nguyen et al. | 604/528 |
| 8,376,991 B2 | * | 2/2013 | Kauphusman et al. | 604/95.04 |
| 8,529,504 B2 | * | 9/2013 | Gibson et al. | 604/95.04 |
| 2002/0161353 A1 | * | 10/2002 | Kortelling | 604/528 |
| 2003/0004493 A1 | | 1/2003 | Casey et al. | |
| 2003/0045831 A1 | | 3/2003 | Ponzi et al. | |
| 2006/0135961 A1 | * | 6/2006 | Rosenman et al. | 606/108 |
| 2006/0184106 A1 | | 8/2006 | McDaniel et al. | |
| 2006/0184107 A1 | | 8/2006 | Bencini et al. | |
| 2007/0010786 A1 | | 1/2007 | Casey et al. | |
| 2007/0299424 A1 | * | 12/2007 | Cumming et al. | 604/527 |
| 2008/0091169 A1 | * | 4/2008 | Heideman et al. | 604/527 |
| 2008/0139999 A1 | * | 6/2008 | Gibson et al. | 604/95.04 |
| 2008/0161762 A1 | * | 7/2008 | Stehr et al. | 604/264 |
| 2009/0312698 A1 | * | 12/2009 | Farrell et al. | 604/95.04 |
| 2012/0130218 A1 | * | 5/2012 | Kauphusman et al. | 600/373 |
| 2012/0184901 A1 | * | 7/2012 | Nguyen et al. | 604/95.04 |
| 2012/0190927 A1 | * | 7/2012 | Uihlein | 600/149 |
| 2012/0203169 A1 | * | 8/2012 | Tegg | 604/95.04 |
| 2012/0209073 A1 | * | 8/2012 | McWeeney et al. | 600/146 |
| 2012/0277671 A1 | * | 11/2012 | Fuentes | 604/95.04 |
| 2013/0030363 A1 | * | 1/2013 | Wong et al. | 604/95.04 |

FOREIGN PATENT DOCUMENTS

| | | |
|---|---|---|
| EP | 1 690 564 A1 | 8/2006 |
| EP | 1 723 981 A1 | 11/2006 |
| JP | 2006-239414 | 9/2006 |
| WO | WO 2005/113057 A1 | 12/2005 |

OTHER PUBLICATIONS

European Search Report dated Jun. 9, 2006, for European Application No. 06250723.1, in the name of Biosense Webster, completed May 15, 2006, 14 pgs.

Extended European Search Report completed Nov. 20, 2012 and mailed Nov. 29, 2012 for EP Application No. 12189612.0 (15 pages).

English translation of Japanese Patent Office Notification of Reasons for Refusal for Patent Application No. 2010-216552, mailing date of Apr. 22, 2014, 4 pgs.

* cited by examiner

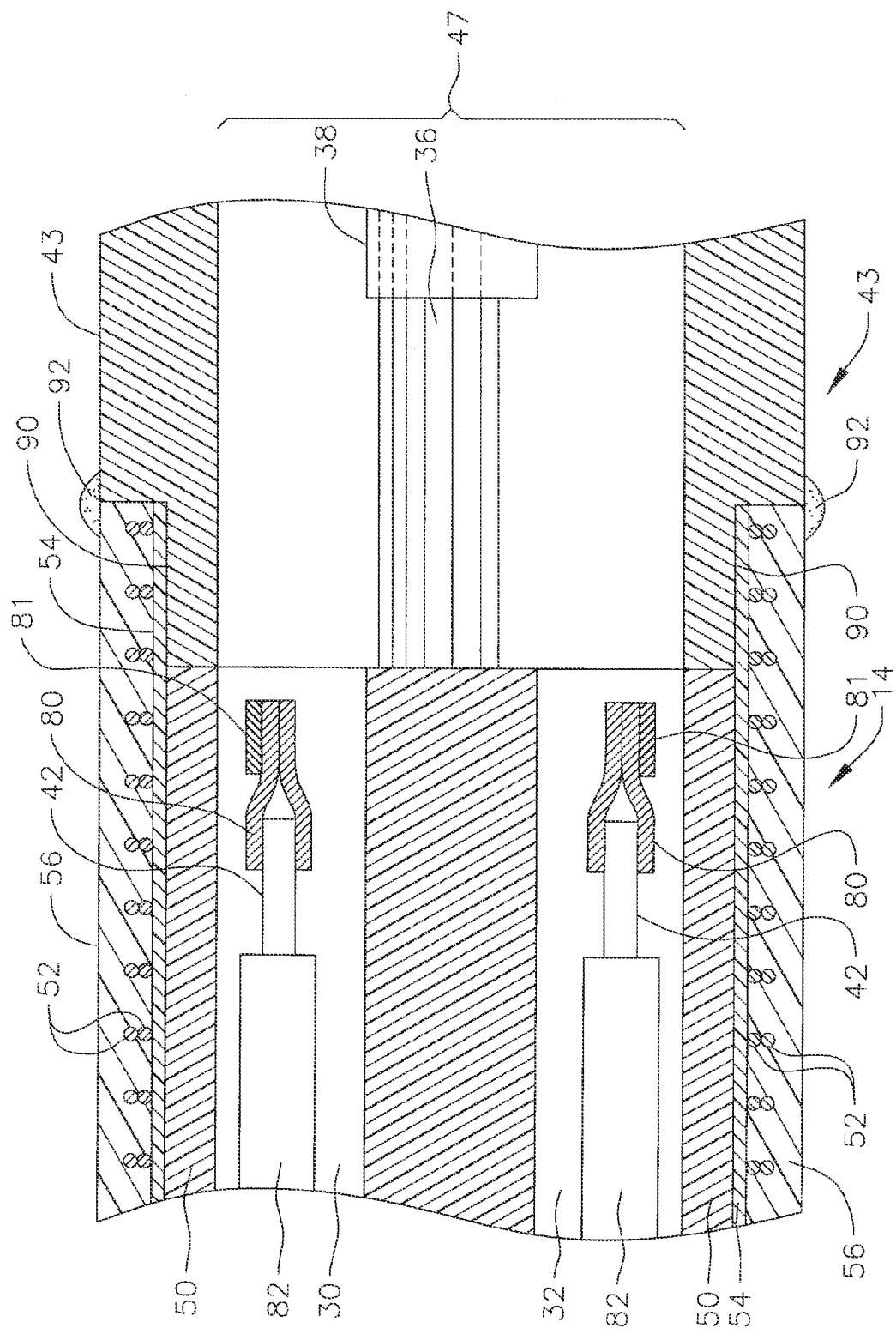

CATHETER WITH BIASED PLANAR DEFLECTION

FIELD OF INVENTION

The present invention relates to an improved steerable catheter, in particular, a catheter with bi-directional deflection for steering a tip section.

BACKGROUND OF INVENTION

Electrode catheters have been in common use in medical practice for many years. They are used to stimulate and map electrical activity in the heart and to ablate sites of aberrant electrical activity.

In use, the electrode catheter is inserted into a major vein or artery, e.g., femoral artery, and then guided into the chamber of the heart which is of concern. Within the heart, the ability to control the exact position and orientation of the catheter tip is critical and largely determines how useful the catheter is.

Steerable (or deflectable) catheters are generally well-known. For example, U.S. Pat. No. RE 34,502 describes a catheter having a control handle comprising a housing having a piston chamber at its distal end. A piston is mounted in the piston chamber and is afforded lengthwise movement. The proximal end of the catheter body is attached to the piston. A puller wire is attached to the housing and extends through the piston and through the catheter body. The distal end of the puller wire is anchored in the tip section of the catheter. In this arrangement, lengthwise movement of the piston relative to the housing results in deflection of the catheter tip section.

Often it is desirable to have a bidirectional steerable catheter, i.e., a catheter that can be deflected in two directions, typically opposing directions. For example, U.S. Pat. No. 6,210,407 discloses a bidirectional steerable catheter having two puller wires extending through the catheter. The distal ends of the puller wires are anchored to opposite sides of the tip section of the catheter. A suitable bidirectional control handle is provided that permits longitudinal movement of each puller wire to thereby allow deflection of the catheter in two opposing directions.

Also known is a steerable catheter having a tip section deflection mechanism is disclosed in U.S. application Ser. No. 11/058,102, filed Feb. 14, 2005, entitled STEERABLE CATHETER WITH IN-PLANE DEFLECTION, the entire disclosure of which is hereby incorporated by reference. However, the deflection mechanism can be improved upon for reinforced tubing, including braided tubing made by the Maypole or sinuous method.

Catheter shafts typically comprise an elongated tubular construction having a single, axial or central lumen. They are flexible, i.e., bendable, but substantially non-compressible along their length. Catheter shafts often have an outer wall made of polyurethane or PEBAX that has an imbedded braided mesh of stainless steel or the like to increase torsional stiffness of the catheter shaft so that rotation at one end (for example, by rotation of a control handle), the shaft will rotate in a corresponding manner through to the other end.

The braided mesh is typically constructed from at least two strands which are wound in oppositely directed helical paths that pass over and under one another in a prescribed sequential interval such as by a maypole or sinuous braiding machine. Maypole-type braiders for the reinforcing of hose and other tubular products and for the production of ropes, cables and the like are known and patented. Patents include U.S. Pat. Nos. 3,371,573, 3,783,736 and 5,257,571, the entire disclosures of which are hereby incorporated by reference.

More modern braiding machines have a mechanism for directing strand supply carrier spindles in intersecting serpentine paths around a braiding point. The mechanism includes a circle of carrier spindle drivers, where each carrier spindle has independent rotation from the driver it is driven thereby so that there is no abrupt change of direction of rotation as it is transferred from a rotor rotating in one direction to a rotor rotating in the opposite direction. Moreover, the braider is also configured so that a strand pay-off point of each carrier is maintained substantially on a line drawn through the center of the spindle and the braiding point during the travel of the carrier spindles in their serpentine paths around the braiding point. Suitable braiding machines for manufacturing reinforced tubing are available from Steeger USA, Inman, S.C., USA.

Although braided and reinforced tubing, and catheter shafts constructed therefrom have better torsional characteristics which minimize kinking and twisting of the shafts, there is need for a tubing construction that integrates the various layers and reinforcement components with a biasing mechanism to promote in-plane deflection, that is, where deflection of at least a portion of the shaft is in the same plane in which the pair of puller wires span. Such a catheter would have greater resistance to out-of-plane deflections to provide more predicable and precise steering of the catheter tip. Accordingly, a need exists for a catheter having an integrated tubing construction that is biased for in-plane bi-directional deflection.

SUMMARY OF THE INVENTION

The present invention is directed to an improved steerable catheter that is biased for in-plane, bi-directional deflection. In one embodiment, the catheter has an elongated catheter body, a deflectable intermediate section having at least two generally diametrically opposing lumens, each carrying a puller wire, and a control handle at a proximal end of the catheter body. In accordance with a feature of the present invention, the intermediate section has an integrated tubing construction with at least two bias members that extend along the length of the intermediate section at generally opposing locations defining between them a transverse axis (or diameter) across the intermediate section. Advantageously, under the influence of the bias members the intermediate section exhibits a more planar deflection relative to a pair of puller wires by which the intermediate section is deflected via the control handle. Thus, a tip section that is distal the intermediate section and carries a tip ablation electrode and/or sensing ring electrode(s) can be more precisely controlled and steered during tissue mapping and ablation.

In a more detailed embodiment, the integrated tubular construction includes an inner layer, a braided mesh surrounding the inner layer and an outer layer, where the bias members is integrated between the inner layer and the braided mesh or between the braided mesh and the outer layer. In another more detailed embodiment, the bias members are wires constructed of metal, metal alloys, stainless steel, nitinol, ceramic, carbon, plastics, and/or combinations thereof.

In another embodiment, the catheter includes a distal tip section having a tip electrode adapted for tissue ablation. The catheter may also include ring electrodes for mapping, an electromagnetic position sensor for determining location of the tip section and/or thermocouple wires for sensing temperature at the tip. The tip section may also be adapted for irrigation by fluid as fed by an irrigation tubing that extends along the catheter to deliver fluid to the tip electrode.

BRIEF DESCRIPTION OF THE DRAWINGS

These and other features and advantages of the present invention will be better understood by reference to the following detailed description when considered in conjunction with the accompanying drawings wherein:

FIG. 6A is a side cross-sectional view of a junction of a deflectable intermediate section and a connective tubing taken along the first diameter of the catheter of FIG. 1

DETAILED DESCRIPTION OF THE INVENTION

Figure 1:
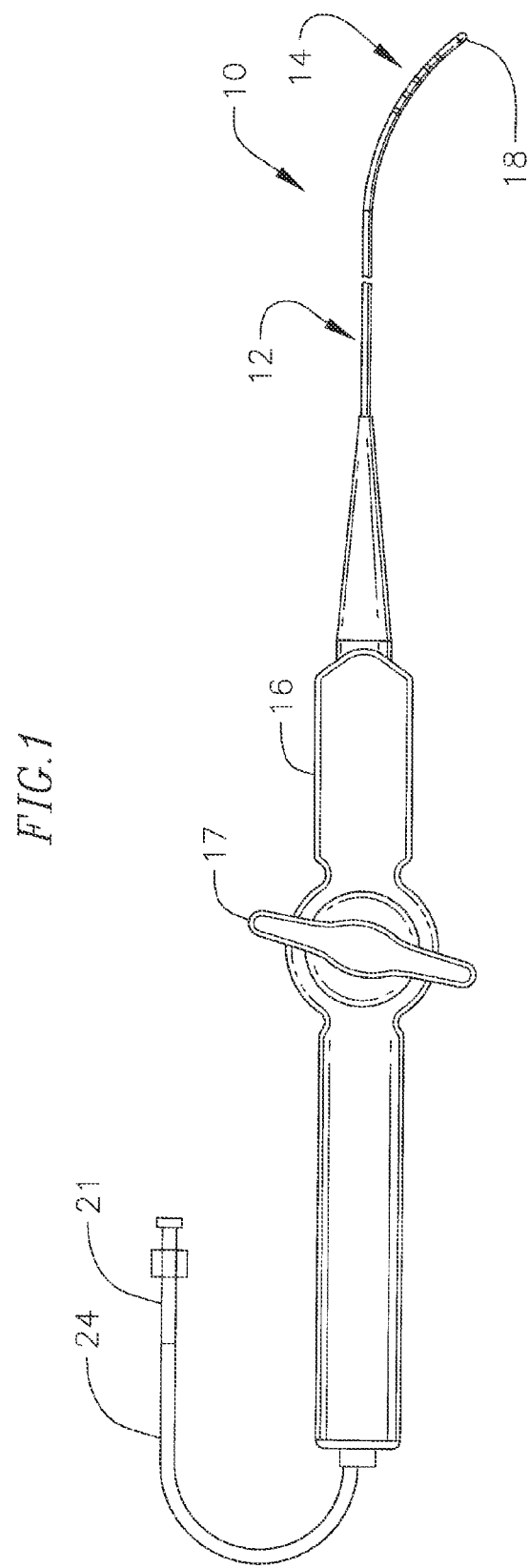
FIG. 1 is a side view of an embodiment of a catheter in accordance with the present invention.

In accordance with a feature of the present invention, there is provided a steerable electrode catheter with mapping and/or ablation capabilities, wherein at least a section of the catheter is biased for in-plane bi-directional deflection. As shown in the embodiment of FIG. 1, the catheter 10 comprises an elongated catheter body 12, a deflectable intermediate section 14 extending from a distal end of the catheter body 12, and a tip section 18 extending from a distal end of the intermediate section 14. A control handle 16 is provided at a proximal end of the catheter body 12. Examples of suitable control handles for use in the present invention are described in U.S. Pat. Nos. 5,897,529, 6,913,594, and 7,377,906, the entire disclosures of which are incorporated herein by reference. In the illustrated embodiment, the control handle 16 has a deflection knob 17 by which an operator can steer the tip section 18 via bi-directional, in-plane deflection of the intermediate section 14.

Figure 2A:
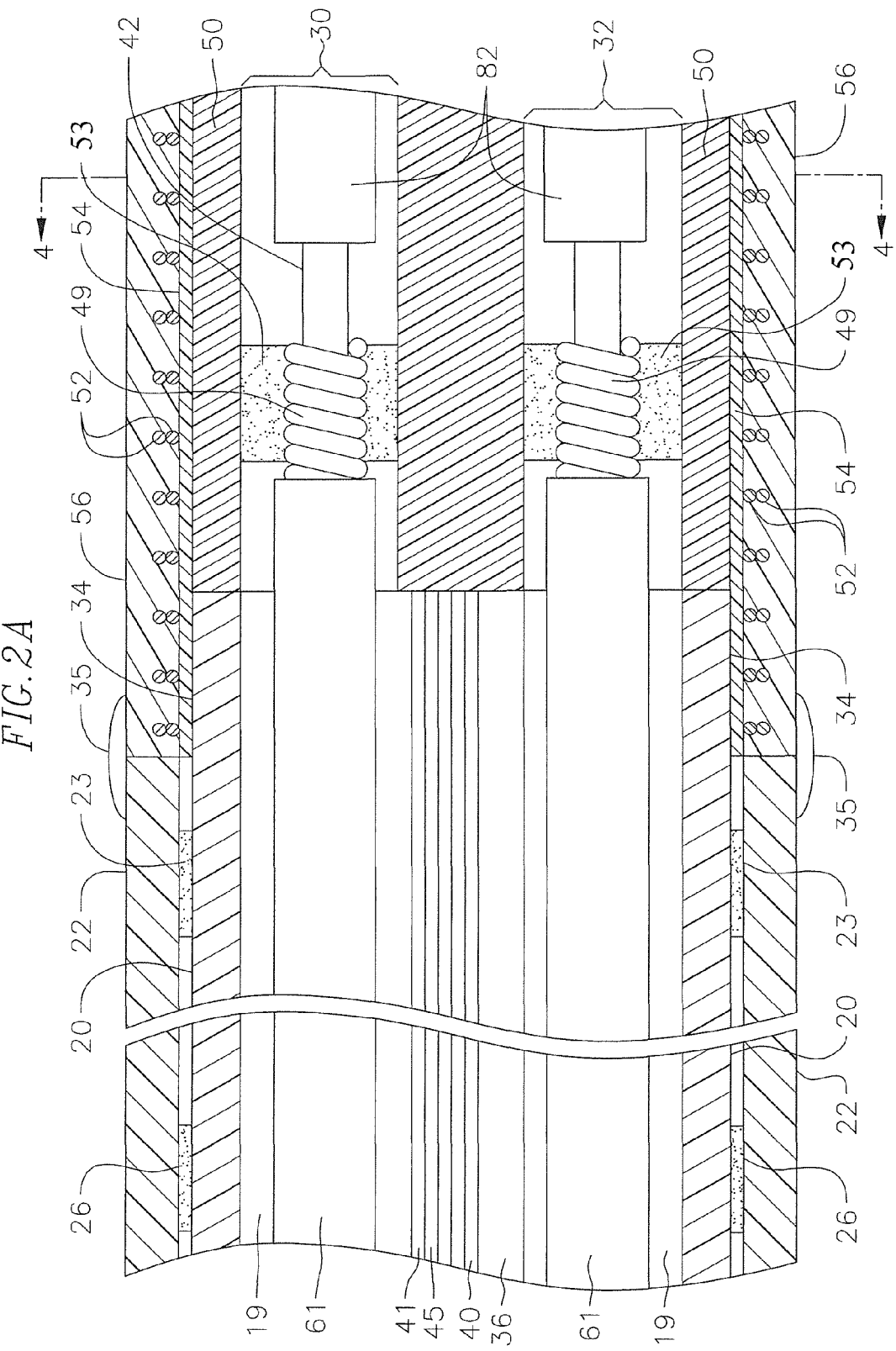
FIG. 2A is a side cross-sectional view of a junction of a catheter body and a deflectable intermediate section taken along a first diameter of the catheter of FIG. 1.
Figure 2B:
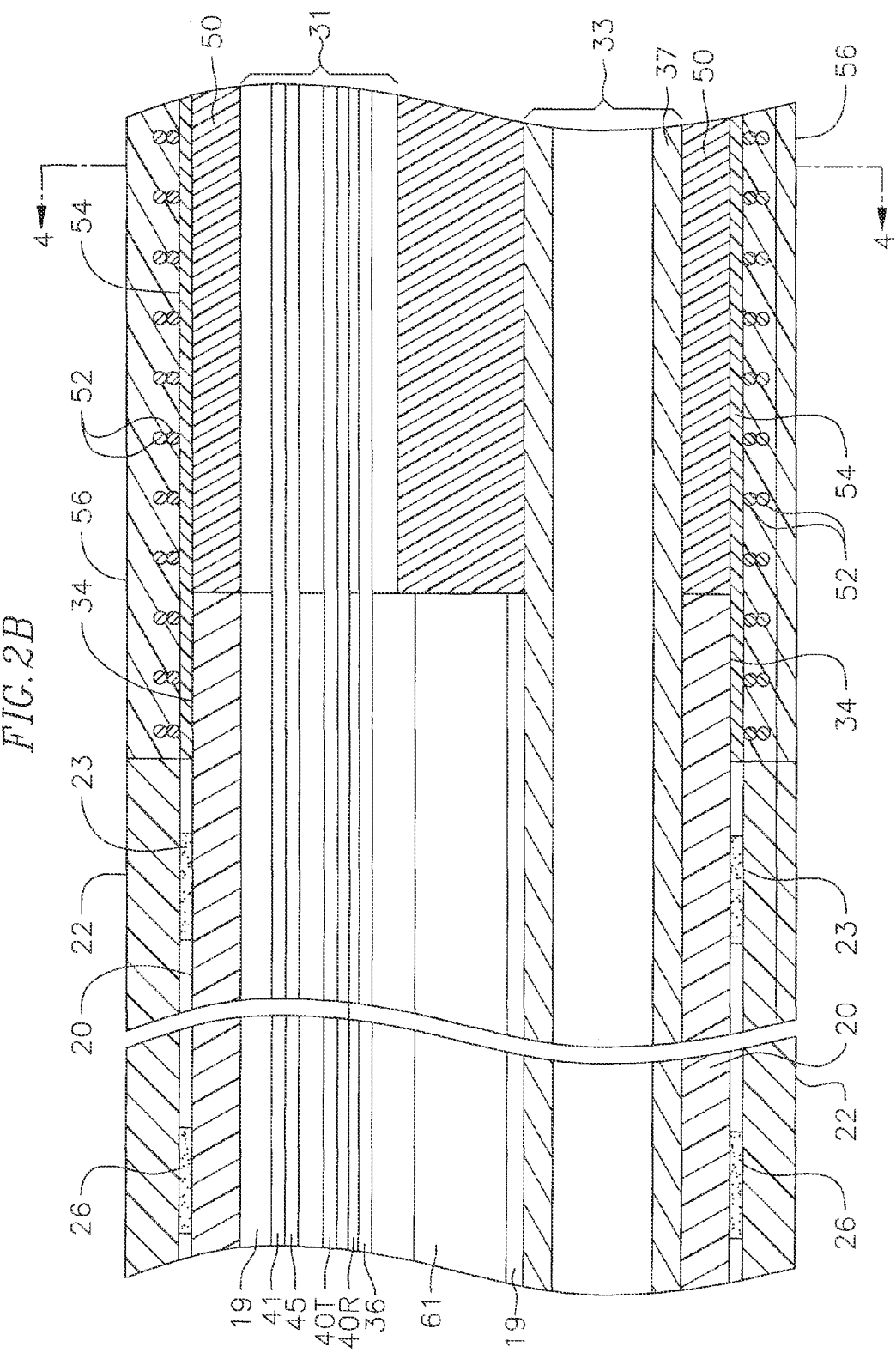
FIG. 2B is a side cross-sectional view of the junction of FIG. 2A taken along a second diameter generally perpendicular to the first diameter.

With reference to FIGS. 2A and 2B, the catheter body 12 comprises an elongated tubular construction having a single, central or axial lumen 19. The catheter body 12 is flexible, i.e., bendable, but substantially non-compressible along its length. The catheter body 12 can be of any suitable construction and made of any suitable material. A presently preferred construction comprises an outer wall 22 made of a polyurethane or nylon. The outer wall 22 comprises an imbedded braided mesh of stainless steel or the like (not shown) to increase torsional stiffness of the catheter body 12 so that, when the control handle 16 is rotated, the tip sectional of the catheter 10 will rotate in a corresponding manner.

The outer diameter of the catheter body 12 is not critical, but is preferably no more than about 8 french. Likewise the thickness of the outer wall 22 is not critical. The inner surface of the outer wall 22 is lined with a stiffening tube 20, which can be made of any suitable material, preferably polyimide. The stiffening tube, along with the braided outer wall 22, provides improved torsional stability while at the same time minimizing the wall thickness of the catheter, thus maximizing the diameter of the single lumen. The outer diameter of the stiffening tube 20 is about the same as or slightly smaller than the inner diameter of the outer wall 22. Polyimide tubing is one preferred material because it may be very thin walled while still providing very good stiffness. This maximizes the diameter of the central lumen 19 without sacrificing strength and stiffness. Polyimide material is typically not used for stiffening tubes because of its tendency to kink when bent. However, it has been found that, in combination with an outer wall 22 of polyurethane, nylon or other similar material, particularly having a stainless steel braided mesh, the tendency for the polyimide stiffening tube 20 to kink when bent is essentially eliminated with respect to the applications for which the catheter is used.

In one embodiment, the catheter has an outer wall 22 with an outer diameter of about 0.092 inch and an inner diameter of about 0.063 inch and a polyimide stiffening tube having an outer diameter of about 0.0615 inch and an inner diameter of about 0.052 inch.

In one embodiment, a first glue joint 23 is made between the stiffening tube 20 and the outer wall 22 by a fast drying glue, e.g. cyanoacrylate. Thereafter a second glue joint 26 is formed between the proximal ends of the stiffening tube 20 and outer wall 22 using a slower drying but stronger glue, e.g., polyurethane.

As illustrated in FIGS. 2A and 2B, the deflectable intermediate section 14 extends from a distal end of the catheter body 12. The intermediate section 14 is configured with multiple off axis lumens 30, 31, 32 and 33, as described further below, for carrying various components, including two puller wires 42 to enable deflection. Other components include lead wires 40, thermocouple wires 41 and 45, a sensor cable 36 and irrigation tubing 37.

Figure 3A:
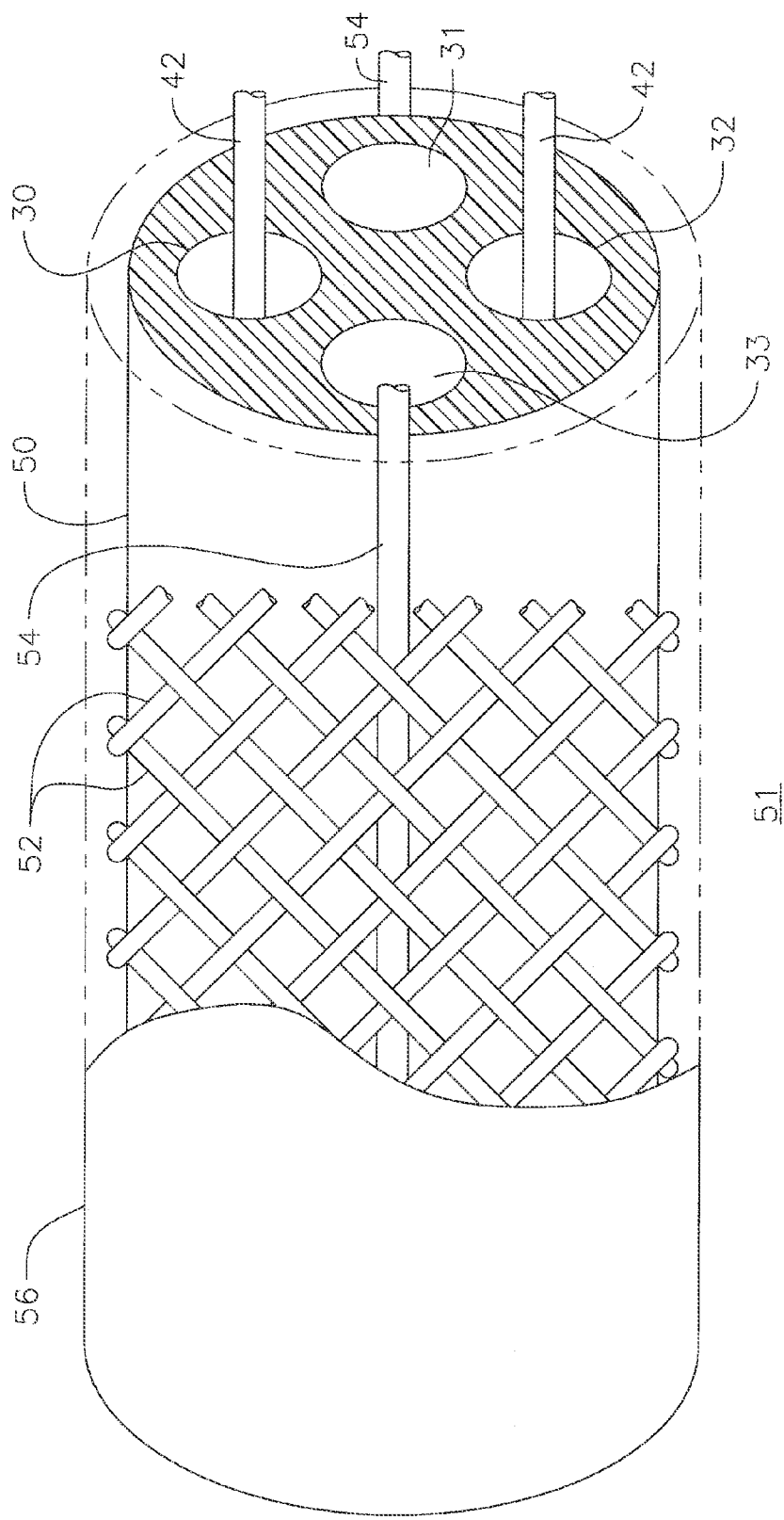
FIG. 3A is an isometric view of an embodiment of an integrated tubular construction biased for in-plane bi-directional deflection, with portions broken away.

With further reference to FIG. 3A, one embodiment of the intermediate section 14 has an integrated tubing construction 51 having an inner layer 50, a reinforcing or braided mesh 52, a pair of bias members 54, and an outer wall 56. In one detailed embodiment, the inner layer 50 includes a melt extrudable polymeric material, e.g., nylon or polyimide, and the outer wall 56 includes a melt extrudable polymeric material, e.g., nylon, polyurethane or PEBAX. Both materials are preferably extruded using known melt or paste extrusion techniques. The inner layer 50 has a wall thickness between about 0.001 and 0.080 inches, preferably between about 0.003 and 0.040 inches, and more preferably between about 0.006 and 0.022 inches. The outer wall 56 has a wall thickness between about 0.001 and 0.050 inches, preferably between about 0.003 and 0.035 inches, and more preferably between about 0.005 and 0.015 inches.

The braided mesh 52 can be applied over the inner layer 50 through the use of a braiding machine well known in the art. The machine includes a plurality of spools of which carry the strands or fibers which are woven or braided. The fibers are fed through the machine to a braiding area in which the fibers are braided or wound about the inner layer 50. Alternatively, the braided mesh 52 also can be constructed in a pre-made, sock-like fashion which is then mounted on the inner layer 50. The strands or fibers of the braided mesh can be flat wire or sheet wire made of metal, plastic, ceramic or glass that is flexible at least a high modulus of elasticity, if not shape memory and/or superelastic properties. In one detailed embodiment, the material should have a high percentage of strain before the material yields. Some suitable materials include stainless steel, Nitinol, and metastable titanium-molybdenum base alloy, and combinations thereof. Other suitable materials include boron ceramic fibers, carbon fiber, and fiberglass. Suitable plastics include aramid fibers, polyester fibers, liquid crystal polymer fibers, such as KEVLAR, NOMEX, DACRON, SPECTRA and VECTRAN.

In one embodiment, the braided mesh 52 comprises interwoven helical members, typically twelve, sixteen or twenty-four interwoven helical members, half extending in one direction and the other half extending in the counter direction. The tightness or braid angle of the helical members to a line parallel with the axis of the catheter and intersecting the helical members is not critical, but is preferably about 45 degrees.

Figure 4:
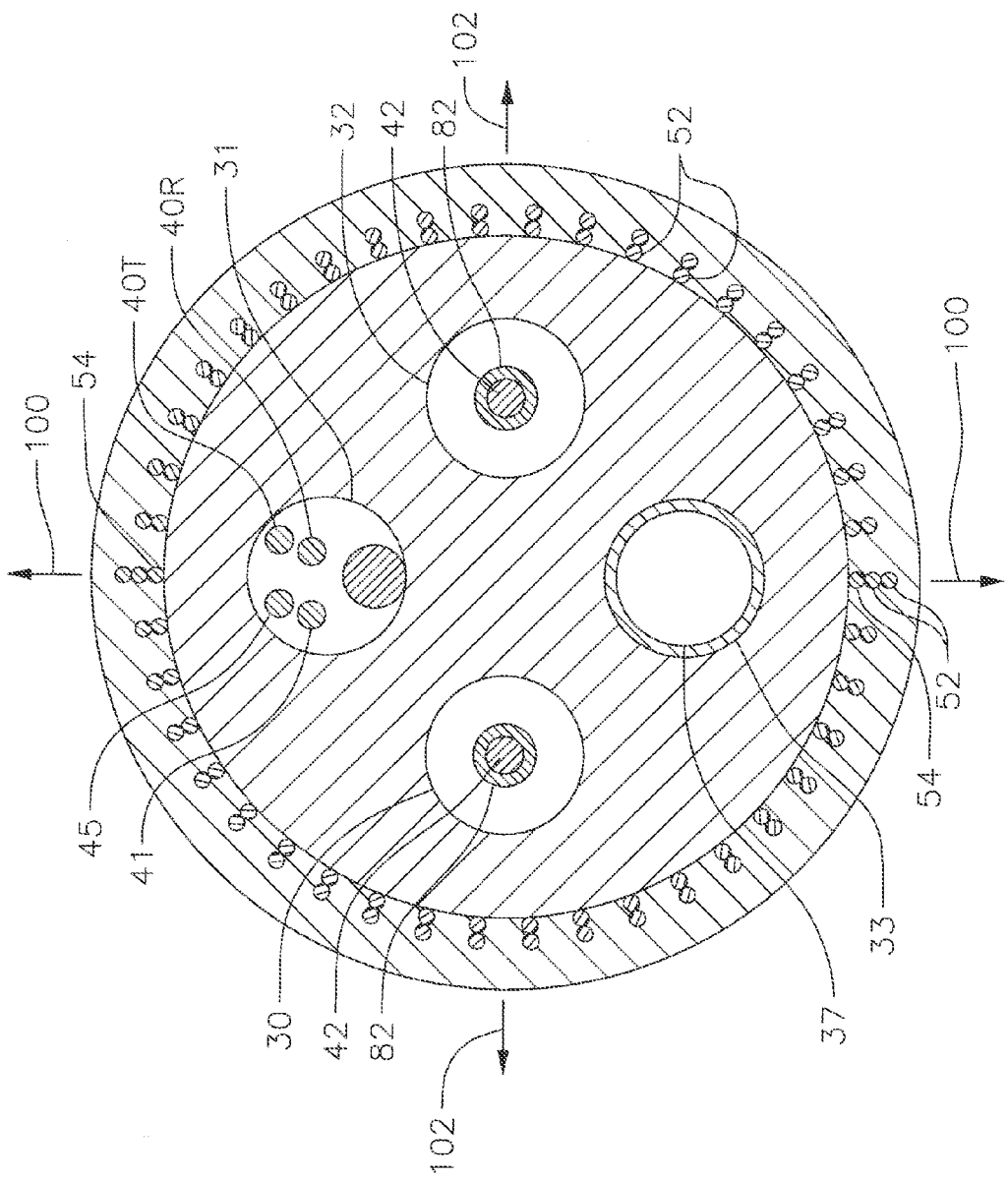
FIG. 4 is a longitudinal cross-sectional view of the deflectable intermediate section of FIGS. 2A and 2B taken along line 4-4.
Figure 5:
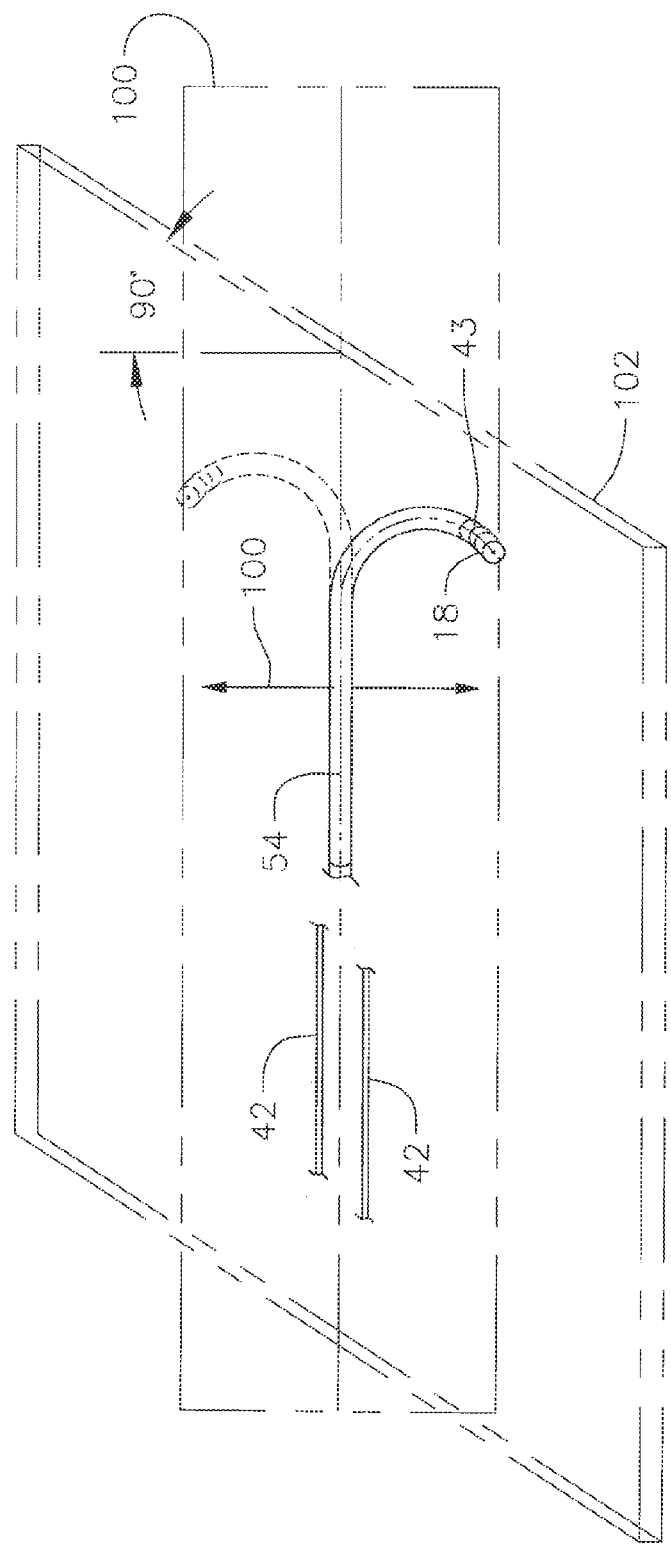
FIG. 5 is a schematic isometric view of the orientation of puller wires relative to a deflected tubing section illustrating in-plane deflection in accordance with a feature of the present invention.

In the illustrated embodiment of FIGS. 3A and 4, there are two elongated bias members or wires 54, each of which is positioned at an opposite side of the intermediate section 14 and extends along the length of the section 14 between the inner layer 50 and the braided mesh 52. Opposing each other across a diameter of the tubing construction, the bias members 54 define a transverse axis or plane 100 that runs along the longitudinal axis of the intermediate section 14, the significance of which is discussed further below. The bias members 54 can be wires made of stainless steel with or without shape memory (e.g., nitinol) and any other suitable material such as those used for the braided mesh 52. Additional suitable materials include ceramic, carbon fiber, metallic elements, alloys, plastics, or combinations thereof.

The extrusion of the outer wall 56 on the inner layer 50, the bias members 54 and the braided mesh 52 integrates or otherwise bonds the bias members 54 and the braided mesh 52 to the inner layer 50. That is, when extruded, the material extruded to form the outer wall 56 melts and flows into the gaps or interstitual spaces of the braided mesh 52 and the bias members 54 which integrally forms them to the inner layer 50 for a layered but integrated construction. Accordingly, relative movement between the braided mesh 52, the bias members 54 and the inner layer 50 is minimal, if any, to provide improved flexural and torsional stability along the intermediate section 14. In particular, the generally diametrically opposing arrangement of the integrated bias members 54 resists flexing of the tubing construction in the plane 100 which in turn biases the tubing construction to flex in a plane that is perpendicular to the plane 100.

In the disclosed embodiment, the cross-section of each of the pair of bias members 54 is generally identical in shape and size for symmetrical bias. The illustrated cross-sectional shape is circular but it is understood that the shape can be any suitable shape, including triangular, rectangular or any other polygonal shape. It is also understood that the cross-section shape of each pair need not be identical in size or shape to each other. Moreover, more than two bias members can be used and the arrangement can be asymmetrical, for example, with two weaker bias members on one side and a single stronger bias member on the other, so the overall or combined effect is balanced or purposefully unbalanced. Furthermore, the bias member(s) need not extend linearly along the length of the affected catheter, that is, the bias members can sinuate or have obtuse or acute angles to impart nonlinear deflection characteristics to the catheter. It is understood that depending on the application of the catheter shaft, the plurality, shape and/or size of the bias members can differ for different deflection characteristic, including a spiral or corkscrew deflection configuration.

In the illustrated embodiment of FIGS. 3A and 4, the inner layer 50 provides multiple off-axis lumens, including the lumens 30, 31, 32 and 33. As illustrated in FIG. 4, the second lumen 31 carries the lead wires 40T and 40R, respectively, for a tip electrode 46 and ring electrode(s) 48, the thermocouple wires 41 and 45 and the cable 36 for an electromagnetic location sensor 38 housed in the tip section 18. The fourth lumen 33 carries an irrigation tubing 37 to transport fluid along the catheter, including fluid to the tip section 18.

In accordance with a feature of the present invention, the first and third lumens 30 and 32 are dedicated to carrying the puller member or wires 42, because a plane 102 in which these lumens lie purposefully perpendicular to the transverse plane 100 defined by the bias members 54. With the bias members 54 resisting flexure of the intermediate section 14 in the plane 100, the intermediate section 14 is biased to exhibit a more planar movement within the plane 102 when deflected by the puller wires 42, thus promoting "in-plane" deflection, that is, deflection within the plane defined by the lumens 30 and 32 and the puller wires 42.

With the intermediate section 14 so configured, movement of the puller wires 42 by an operator's manipulation of the control handle 16 allows for more predictable bi-directional deflection of the intermediate section 14 and hence more precise control and steering of the tip section 18 during ablation and/or mapping. It is understood that the precise size of the lumens is not critical and will depend on the sizes of the components being carried by the lumens.

Means for attaching the catheter body 12 to the intermediate section 14 is illustrated in FIGS. 2A and 2B. The proximal end of the intermediate section 14 comprises an outer circumferential notch 34 between the inner layer 50 and the outer layer 56 that receives the inner surface of the outer wall 22 of the catheter body 12. This junction may be secured by glue or the like 35.

If desired, a spacer (not shown) can be located within the catheter body between the distal end of the stiffening tube 22 (if provided) and the proximal end of the intermediate section 14. The spacer provides a transition in flexibility at the junction of the catheter body 12 and intermediate section 14, which allows this junction to bend smoothly without folding or kinking. A catheter having such a spacer is described in U.S. Pat. No. 5,964,757, the disclosure of which is incorporated herein by reference.

At the distal end of the intermediate section 14 is the tip section 18 that is connected to intermediate section by a connective tubing 43. In the illustrated embodiment of FIGS. 6a and 6b, the connective tubing 43 has a single lumen 47 which allows passage of the lead wires 40T and 40R, the thermocouple wires 41 and 45, the electromagnetic sensor cable 36 and the irrigation tubing 37 from the intermediate section 14 to the tip section 18. The single lumen 47 allows these components to reorient themselves from their respective lumens in the intermediate section 14 toward their location in the tip section 18. As shown, various components can criss-cross each other to align themselves properly within the tip section 18.

Figure 6B:
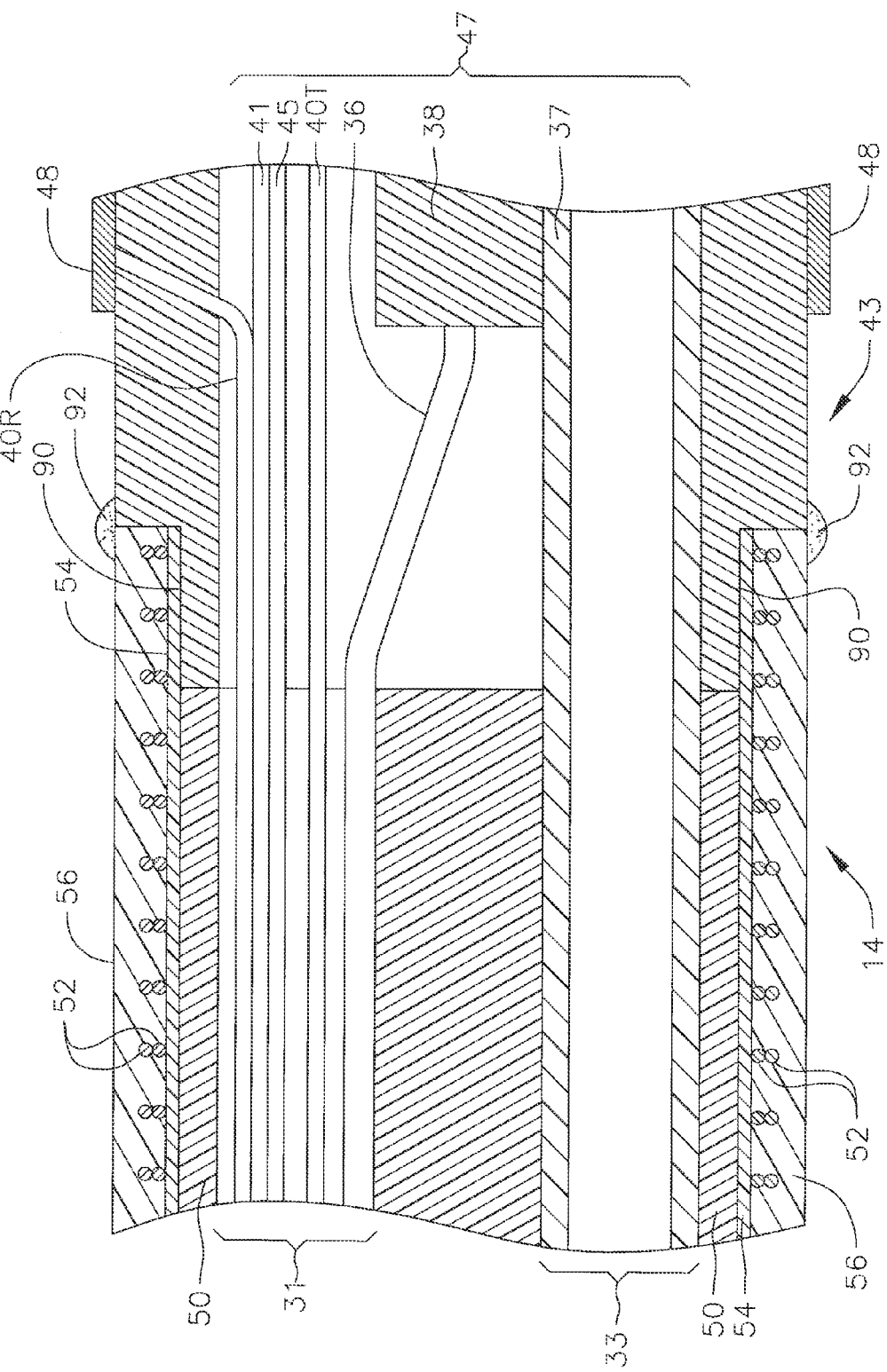
FIG. 6B is a side cross-sectional view of the junction of FIG. 6A, taken along the second diameter.

Means for attaching the intermediate section 14 to the connective tubing 43 is illustrated in FIGS. 6A and 6B. The proximal end of the connective tubing 43 comprises an outer circumferential notch 90 that receives the inner surface of the tubing construction 51 between the outer layer 56 and the inner layer 50. This junction may be secured by glue or the like 92.

Figure 7:
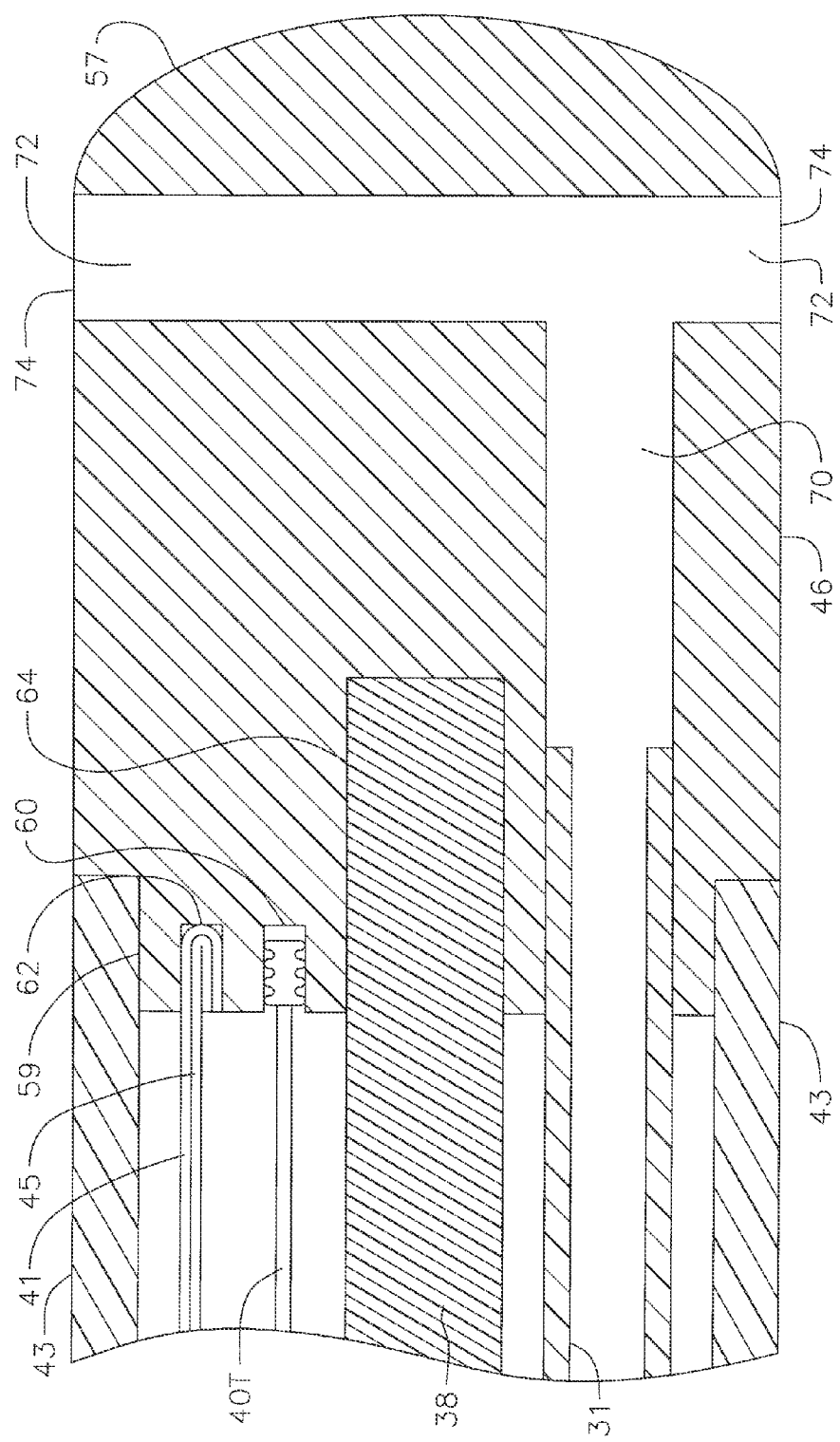
FIG. 7 is a side cross sectional view of a tip section of the catheter of FIG. 1, taken along the second diameter.

The tip electrode 46 as shown in FIG. 7 has a distal end 57 configured with an atraumatic design for contact with tissue and tissue ablation as appropriate. Received in a distal end of the connective tubing 43, a trepanned proximal end 59 of the tip electrode has a proximal surface in which blind holes 60, 62 and 64 are configured for receiving, respectively, a distal end of a lead wire 40T for the energizing the tip electrode, distal ends of the thermocouple wires 41 and 45 for sensing temperature at the tip electrode, and a distal end of the electromagnetic sensor 38. These distal ends are anchored in the blind holes as known in the art. A fluid passage 70 is formed in the tip electrode extending along its longitudinal axis. A proximal end of the fluid passage receives a distal end of the irrigation tubing 37 which is adapted to transport fluid into the fluid passage 70. Transverse branches 72 are provided to allow fluid to travel outside the tip electrode via ports 74 to, for example, irrigate and cool the tip electrode 46 and/or the ablation tissue site. Proximal the tip electrode 46, one or more ring electrodes 48 (uni-polar or bi-polar for mapping) can be mounted on the connective tubing 43, each with a respective lead wire 40R.

The ring electrode(s) 48 are connected to lead wires 40R and the tip electrode 46 is connected to lead wire 40T. The lead wires 40T and 40R extend proximally from the tip section 18 through the lumen 47 of the connective tubing 43, the lumen 31 of the intermediate section 14, the central lumen 19 of the catheter body 12, and the control handle 16, and terminate at their proximal end in a connector (not shown) so that signals can be sent to an appropriate signal processing unit (not shown) and the electrodes can be connected to a source of ablation energy (not shown), including RF. The portion of the lead wires extending through the central lumen 19 of the catheter body 12, and proximal end of the second lumen 31 can be enclosed within a protective sheath (not shown), which can be made of any suitable material, preferably polyimide. The protective sheath is anchored at its distal end to the proximal end of the intermediate section 14 by gluing it in the lumen 31 with polyurethane glue or the like.

Each lead wire 40R is attached to its corresponding ring electrode by any suitable method. A preferred method for attaching a lead wire to a ring electrode 48 involves first making a small hole through the wall of the connective tubing 43. Such a hole can be created, for example, by inserting a needle through the non-conductive covering sufficiently to form a permanent hole. The lead wire is then drawn through the hole by using a microhook or the like. The end of the lead wire is then stripped of any coating and welded to the underside of the ring electrode, which is then slid into position over the hole and fixed in place with polyurethane glue or the like. Alternatively, each ring electrode is formed by wrapping a lead wire around the non-conductive covering a number of times and stripping the lead wire of its own insulated coating on its outwardly facing surfaces. More alternatively, the ring electrodes can be formed by coating the tubing with an electrically conducting material, like platinum, gold and/or iridium. The coating can be applied using sputtering, ion beam deposition or an equivalent technique.

The thermocouple wires 41 and 45 extend from their distal ends anchored in the tip electrode 46, through the single lumen 47 of the connective tubing 43, through the second lumen 31 of the intermediate section 14, through the central lumen 19 of the catheter body 12, and into the control handle 16 where its proximal end terminates in the connector 90 at the proximal end of the control handle 16.

The cable 36 of the electromagnetic position sensor 38 extends proximally through the lumen 47 of the connective tubing 43, through the second lumen 31 of the intermediate section 14, through the central lumen 19 of the catheter body 12, and into the control handle 16. The electromagnetic sensor cable 36 comprises multiple wires encased within a plastic covered sheath. In the control handle 16, the sensor cable 36 is connected to a circuit board (not shown). The circuit board amplifies the signal received from the electromagnetic sensor and transmits it to a computer in a form a understandable by the computer. Suitable electromagnetic sensors for use with the present invention are described, for example, in U.S. patent application Ser. No. 09/160,063 (entitled "Miniaturized Position Sensor") and U.S. Pat. Nos. 5,558,091, 5,443,489, 5,480,422, 5,546,951, 5,568,809, and 5,391,199, the disclosures of which are incorporated herein by reference.

The irrigation tubing 37 extends proximally from the tip electrode 46 through the central lumen 47 of the connective tubing 43, through the fourth lumen 33 of the intermediate section 14, through the central lumen 19 of the catheter body 12 and through the control handle 16. Saline or other suitable fluid is introduced into the irrigation tubing 37 through a luer hub 21 or the like at the proximal end of the control handle 16. The luer hub 21 is connected to a flexible plastic tubing 24, e.g., made of polyimide. The plastic tubing 24 is attached to the proximal end of the irrigation tubing, preferably within the handle 16, as shown in FIG. 1. Alternatively, the tubing 24 can be connected to a suction source (not shown) to permit aspiration of fluid from the region being ablated.

Each puller wire 42 extends from the control handle 16, through the central lumen 19 in the catheter body 12 and into a different one of the first and third lumens 30 and 32 of the inner layer 50 of the intermediate section 14, as shown in FIGS. 2A and 6A. The puller wires 42 is made of any suitable material, such as stainless steel or Nitinol. Preferably each puller wire has a coating, such as a coating of Teflon® or the like. Each puller wire has a diameter preferably ranging from about 0.006 inch to about 0.0010 inch. Both of the puller wires have the same diameter.

Each puller wire 42 is anchored at its proximal end in the control handle 16 such that manipulation of controls, for example, the deflection knob 17, moves the puller wires to cause deflection of the intermediate section 14. In that regard, each puller wire is anchored at its distal end in a side wall at or near a distal end of the intermediate section 14 by means of a T-bar anchor constructed of a metal tube 80, e.g., a short segment of hypodermic stock, which is fixedly attached, e.g., by crimping, to the distal end of the puller wire, and a crosspiece 81 soldered or welded in a transverse arrangement to a flattened distal end of the tube 80. T-bar anchors are described in U.S. Pat. Nos. 6,267,746 and 6,064,908, the entire disclosures of which are hereby incorporated by reference. Other means for anchoring the puller wires 42 in the intermediate section 14 would be recognized by those skilled in the art and are included within the scope of the invention, including anchoring the distal end in blind holes provided at the proximal end of the tip electrode 46.

The disclosed embodiment of the catheter 10 further comprises two compression coils 49, each in surrounding relation to a corresponding puller wire 42 in the catheter body 12, as shown in FIGS. 2A and 2B. In the illustrated embodiment, each compression coil is made of any suitable metal, such as stainless steel, and is tightly wound on itself to provide flexibility, i.e., bending, but to resist compression. The inner diameter of each compression coil is slightly larger than the diameter of its associated puller wire 42. For example, when a puller wire 42 has a diameter of about 0.007 inch, the corresponding compression coil 49 preferably has an inner diameter of about 0.008 inch. A coating on the puller wires 42 allows them to slide freely within the compression coil 49. The outer surface of each compression coil 49 is covered along most of its length by a flexible, non-conductive sheath 61 to prevent contact between the compression coil 49 and the lead wire(s) 40 within the central lumen 19. In one embodiment, the non-conductive sheath 61 is made of thin-walled polyimide tubing.

The compression coils 49 are secured within the catheter body 12 with polyurethane glue or the like. Each compression coil 49 is anchored at its proximal end to the proximal end of the stiffening tube 22 in the catheter body 12 by a glue joint (not shown). In the depicted embodiment of FIG. 2A, the distal ends of the compression coils 49 extend into the lumens 30 and 32 of the intermediate section 14 and are anchored at their distal ends to the proximal end of the intermediate section by a glue joint 53. Alternatively, where a stiffening tube 22 is not used, each compression coil at its proximal and distal ends can be anchored directly to the outer wall 20 of the catheter body 12.

In the embodiment of FIGS. 2A and 6A, within the off-axis lumens 30 and 32, each puller wire 42 is surrounded by a plastic sheath 82, preferably made of Teflon®. The plastic sheaths 82 prevent the puller wires from cutting into the inner layer 50 of the intermediate section 14 when deflected. Each sheath 82 spans generally the length of the intermediate section 14. Alternatively, each puller wire 42 can be surrounded by a compression coil where the turns are expanded longitudinally, relative to the compression coils extending through the catheter body, such that the surrounding compression coil is both bendable and compressible.

In a detailed embodiment, longitudinal movement of a puller wire 42 relative to the catheter body 12, which results in deflection of the tip section 14 in the direction of the side of the intermediate section to which that puller wire extends, is accomplished by suitable manipulation of the control handle 16. Additional suitable bidirectional control handles for use in the present invention is described in application Ser. No. 09/822,087, filed Mar. 30, 2001 and entitled "Steerable Catheter with a Control Handle Having a Pulley Structure", and in U.S. Pat. Nos. 6,123,699, 6,171,277, 6,198,974, and 7,377,906, the entire disclosures of which are incorporated herein by reference.

As shown in the embodiment of FIG. 4, the lumens 30 and 32 carrying the puller wires 42 lie on the plane 102 that is generally perpendicular to a transverse plane 100 in which the two bias members 54 lie. As such, deflection of the intermediate section 14 as accomplished by longitudinal movement of the puller wires 42 is generally planar in that the intermediate section 14 (along with the tip 18) remains generally within the plane 102.

Figure 3B:
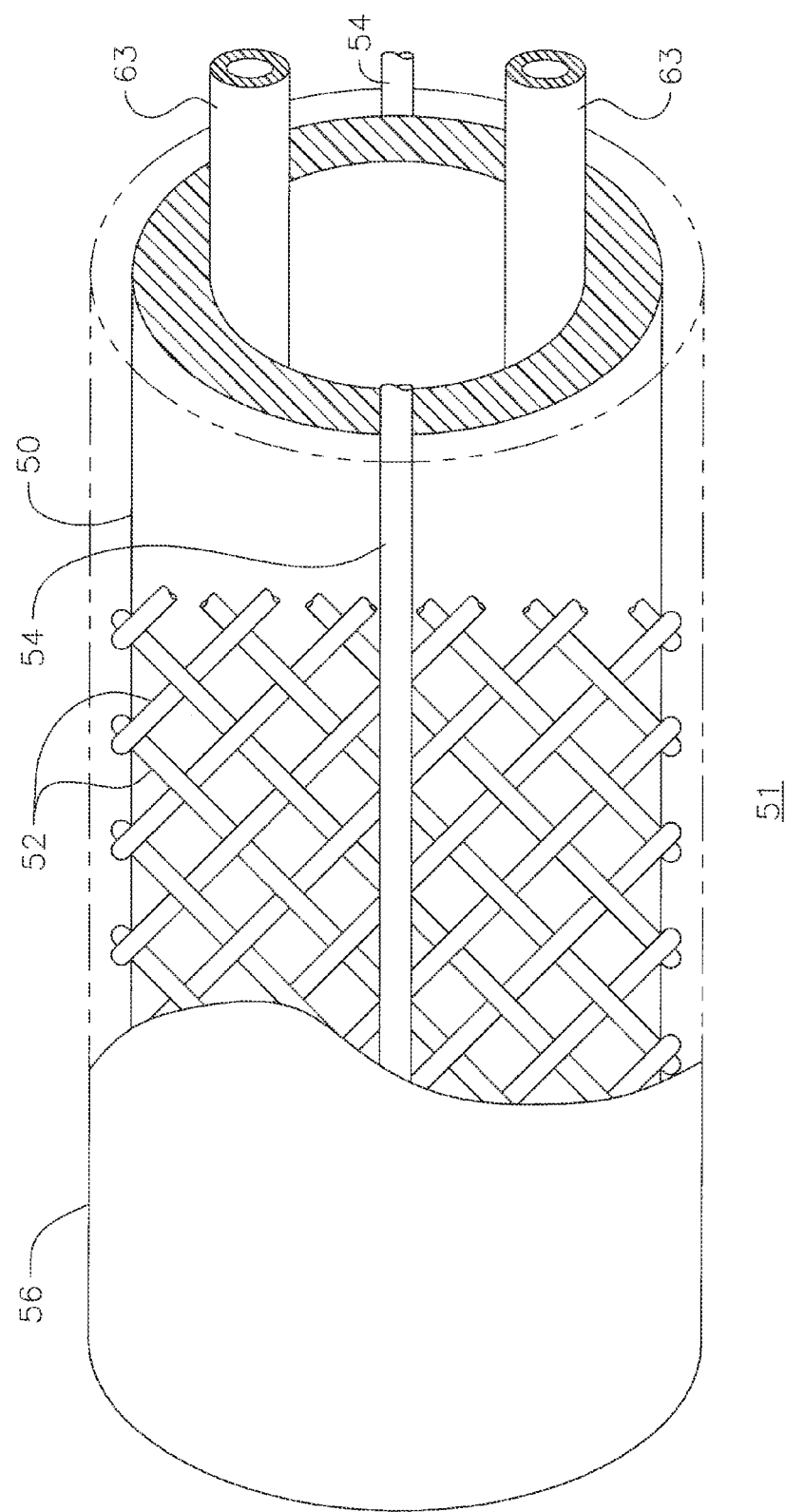
FIG. 3B is an isometric view of an alternate embodiment of an integrated tubular construction biased for in-plane bi-directional deflection, with portions broken away.
Figure 3C:
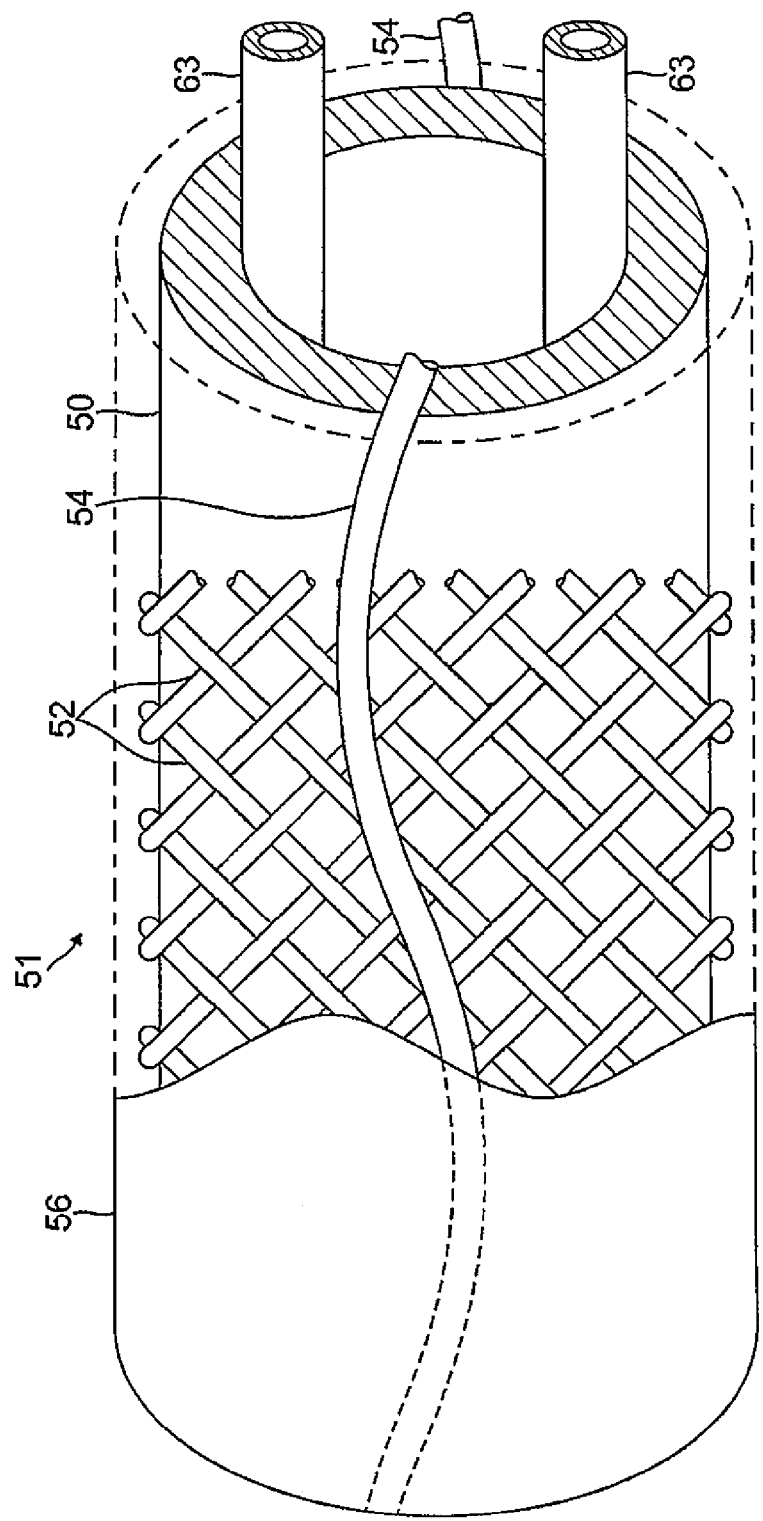
FIG. 3C is an isometric view of an alternate embodiment of an integrated tubular construction biased for in-plane bi-directional deflection, with portions broken away, with elongated bias members extending longitudinally and nonlinearly.

With reference to FIG. 3B, in an alternate embodiment of the integrated tubing construction 51, the bias members 54 can be situated outside of the braided mesh 52 so that the bias members are integrated between the outer wall 56 and the braided mesh 52. Because the outer wall 56 is extruded, the material forming the outer wall melts and flows into the gaps or interstitual spaces of the braided mesh 52 and the bias members 54 which integrally forms them to the inner layer 50.

As another alternate embodiment, the inner layer 50 need not provide multiple lumens, but can be formed with only a central lumen, as shown in FIG. 3B, as desirable or appropriate, such as for a catheter body or any section of the catheter 10, including the deflectable intermediate section where components extending therethrough including the puller wires 42 float in the central lumen or can be routed through separate tubings 63 that are fixedly secured in place within the central lumen by glue or the like.

Relative movement between the braided mesh 52, the bias members 54 and the inner layer 50 is minimal, if any, so as to enable the tubing construction to have a more planar deflection characteristic, yet with all the benefits of flexural and torsional stability. It is further understood that most catheter tubing can be retrofitted with bias members of the present invention. Extrusion of an outer layer over the bias members sufficiently integrates the bias members into the preexisting catheter tubing to provide biased in-plane bi-directional deflection.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention. As understood by one of ordinary skill in the art, the drawings are not necessarily to scale. Accordingly, the foregoing description should not be read as pertaining only to the precise structures described and illustrated in the accompanying drawings, but rather should be read consistent with and as support to the following claims which are to have their fullest and fair scope.

What is claimed is:

1. A steerable catheter comprising:
   an elongated catheter body;
   a deflectable intermediate section comprising an integrated tubing construction with at least two off-axis lumens defining a plane of deflection, the deflectable intermediate section further comprising at least two bias members extending longitudinally and non-linearly along the intermediate section at opposing locations defining a transverse axis that is generally perpendicular to the plane of deflection;
   a first puller wire extending through a first lumen of the at least two off-axis lumens, and a second puller wire extending through a second lumen of the at least two off-axis lumens;
   a control handle at the proximal end of the catheter body;
   wherein the deflectable intermediate section is biased by the bias members to remain generally within the plane of deflection.

2. A catheter of claim 1, wherein the integrated tubing construction comprises an inner layer, a braided mesh surrounding the inner layer, and an outer layer, wherein the bias members are integrated between the inner layer and the braided mesh.

3. A catheter of claim 2, wherein the at least two off-axis lumens are in the inner layer of the integrated tubing construction.

4. A catheter of claim 3, wherein the at least two off-axis lumens comprise at least three lumens.

5. A catheter of claim 1, wherein the integrated tubing construction comprises an inner layer, a braided mesh surrounding the inner layer, and an outer layer, wherein the bias members are integrated between the braided mesh and the outer layer.

6. A catheter of claim 5, wherein the at least two off-axis lumens are in the inner layer of the integrated tubing construction.

7. A catheter of claim 6, wherein the at least two off-axis lumens comprises at least three lumens.

8. A catheter of claim 1, further comprising a tip section distal to the deflectable intermediate section.

9. A catheter of claim 1, wherein the bias members are constructed of a material selected from the group consisting of: metals, metal alloys, stainless steel, nitinol, ceramics, carbon, plastics, and combinations thereof.

10. A catheter comprising:
- an elongated, flexible tubular catheter body having proximal and distal ends and a lumen extending therethrough;
- a deflectable intermediate section at the distal end of the catheter body, the intermediate section comprising a flexible integrated tubing construction having at least one pair of diametrically-opposed lumens defining a first plane;
- a tip section at a distal end of the deflectable intermediate section;
- a control handle at the proximal end of the catheter body;
- first and second puller wires, each of the first and second puller wires extending through a different one of the diametrically-opposed lumens of the deflectable intermediate section and through the lumen of the catheter body, each of the first and second puller wires having a proximal end anchored to the control handle and a distal end anchored at a location at or near the distal end of the deflectable intermediate section, whereby the first and second puller wires are longitudinally moveable relative to the catheter body to cause deflection of the deflectable intermediate section; and
- two elongated bias members, each of the elongated bias members extending non-linearly along the deflectable intermediate section, the two elongated bias members defining a second plane perpendicular to the first plane, wherein the elongated bias members bias the deflectable intermediate section to maintain the perpendicular relationship between the first and second planes when deflected by the puller wires.

11. A catheter of claim 10, wherein the bias members are constructed of a material selected from the group consisting of: metals, metal alloys, stainless steel, nitinol, ceramics, carbon, plastics, and combinations thereof.

12. A catheter of claim 10, wherein the integrated tubing construction comprises an inner layer, a braided mesh surrounding the inner layer, and an outer layer, wherein the bias members are integrated between the inner layer and the braided mesh.

13. A catheter of claim 12, wherein the outer layer is extruded.

14. A catheter of claim 10, wherein the integrated tubing construction comprises an inner layer, a braided mesh surrounding the inner layer, and an outer layer, wherein the bias members are integrated between the braided mesh and the outer layer.

15. A catheter of claim 14, wherein the outer layer is extruded.

16. A catheter of claim 10, wherein the tip section includes a tip electrode adapted for tissue ablation.

17. A catheter of claim 16, wherein the tip electrode is adapted for irrigation of fluid.

18. A catheter of claim 10, wherein the tip section includes at least one ring electrode adapted for mapping.

19. A catheter comprising:
- an elongated catheter body,
- a deflectable section distal to the catheter body, the deflectable section having at least two elongated bias members, the at least two elongated bias members extending non-linearly along opposing locations of the deflectable section and lying on a plane;
- at least one puller wire extending through the catheter body and the deflectable section;
- a tip section distal to the catheter body, the tip section adapted for tissue ablation; and
- a control handle at a proximal end of the catheter body, adapted for manipulation of the puller wire to thereby effect deflection of the deflectable section,
- wherein the at least two elongated bias members resist flexure within the plane when the deflectable section is deflected.

20. A catheter comprising:
- an elongated catheter body,
- a deflectable section distal to the catheter body, the deflectable section including a central lumen, the deflectable section also having at least two elongated bias members, the at least two elongated bias members extending non-linearly along opposing locations of the deflectable section and lying on a plane;
- at least one tubing extending through the central lumen of the deflectable section, the at least one tubing being fixedly attached to an inner wall of the deflectable section defining the central lumen;
- at least one puller member extending through the at least one tubing;
- a tip section distal to the catheter body, the tip section adapted for tissue ablation; and
- a control handle at a proximal end of the catheter body, adapted for manipulation of the at least one puller member to thereby effect deflection of the deflectable section,
- wherein the at least two elongated bias members resist flexure within the plane when the deflectable section is deflected.

* * * * *